United States Patent
Noguchi (10) Patent No.: US 10,111,579 B2
(45) Date of Patent: Oct. 30, 2018

(54) ENDOSCOPE HAVING AN ILLUMINATION SYSTEM SHIFTED WITH RESPECT TO AN IMAGING SYSTEM TO REDUCE GENERATION OF HEAT AT A FRONT-END PORTION OF THE ENDOSCOPE

(71) Applicant: OLYMPUS CORPORATION, Hachioji-shi, Tokyo (JP)

(72) Inventor: Azusa Noguchi, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/673,373

(22) Filed: Aug. 9, 2017

(65) Prior Publication Data
US 2017/0367568 A1 Dec. 28, 2017

Related U.S. Application Data

(63) Continuation of application No. PCT/JP2015/082212, filed on Nov. 17, 2015.

(30) Foreign Application Priority Data

Feb. 9, 2015 (JP) .................................. 2015-022961

(51) Int. Cl.
*A61B 1/06* (2006.01)
*A61B 1/07* (2006.01)
(Continued)

(52) U.S. Cl.
CPC .................. *A61B 1/07* (2013.01); *A61B 1/00* (2013.01); *A61B 1/018* (2013.01); *A61B 1/04* (2013.01);
(Continued)

(58) Field of Classification Search
CPC .... A61B 1/07; A61B 1/05; A61B 1/06; G02B 23/243; G02B 23/2469; G02B 23/2484; G02B 23/2492
(Continued)

(56) References Cited

U.S. PATENT DOCUMENTS 4,017,150 A * 4/1977 Imai .................... A61B 1/00096
385/119
4,802,460 A * 2/1989 Ohkuwa ............ A61B 1/00096
385/117
(Continued)

FOREIGN PATENT DOCUMENTS

JP 08254659 A 10/1996
JP 11326786 A 11/1999
(Continued)

OTHER PUBLICATIONS

International Search Report (ISR) and Written Opinion dated Feb. 9, 2016 issued in International Application No. PCT/JP2015/082212.
(Continued)

*Primary Examiner* — John P Leubecker
(74) *Attorney, Agent, or Firm* — Holtz, Hotlz & Volek PC (57) ABSTRACT

An endoscope includes an imaging system and an illumination system. The illumination system includes a light guide and at least one illumination lens, and the imaging system includes an objective lens unit and an image pickup element. When a direction along a long side of the image pickup element is set to be a first direction, and a direction along a short side of the image pickup element is set to be a second direction, the illumination system is disposed at a position shifted in the second direction with respect to the imaging system.

3 Claims, 8 Drawing Sheets (51) Int. Cl.
- *A61B 1/00* (2006.01)
- *A61B 1/04* (2006.01)
- *G02B 23/24* (2006.01)
- *G02B 23/26* (2006.01)
- *A61B 1/018* (2006.01)
- *A61B 1/05* (2006.01)

(52) U.S. Cl.
CPC .............. *A61B 1/05* (2013.01); *G02B 23/24* (2013.01); *G02B 23/243* (2013.01); *G02B 23/2469* (2013.01); *G02B 23/2484* (2013.01); *G02B 23/2492* (2013.01); *G02B 23/26* (2013.01)

(58) Field of Classification Search
USPC .................................................. 600/177, 182
See application file for complete search history.

(56) References Cited

U.S. PATENT DOCUMENTS

| | | | | |
|---|---|---|---|---|
| 8,777,847 | B2* | 7/2014 | Sato | A61B 1/00137 600/129 |
| 8,961,404 | B2* | 2/2015 | Ito | A61B 1/00091 600/169 |
| 2001/0003142 | A1* | 6/2001 | Koshikawa | A61B 1/00096 600/177 |
| 2011/0245617 | A1 | 10/2011 | Kitano | |
| 2012/0253129 | A1 | 10/2012 | Kitano | |
| 2015/0087904 | A1* | 3/2015 | Takahashi | A61B 1/00181 600/109 |
| 2016/0195706 | A1* | 7/2016 | Fujii | A61B 1/00096 362/551 |
| 2016/0345806 | A1* | 12/2016 | Ishii | A61B 1/005 |
| 2017/0035282 | A1* | 2/2017 | Kaneko | A61B 1/00167 |

FOREIGN PATENT DOCUMENTS

| | | |
|---|---|---|
| JP | 2001292956 A | 10/2001 |
| JP | 2011215425 A | 10/2011 |
| JP | 2012200480 A | 10/2012 |

OTHER PUBLICATIONS

International Preliminary Report on Patentability (IPRP) (and English translation thereof) dated Aug. 24, 2017 issued in counterpart International Application No. PCT/JP2015/082212.

\* cited by examiner

ENDOSCOPE HAVING AN ILLUMINATION SYSTEM SHIFTED WITH RESPECT TO AN IMAGING SYSTEM TO REDUCE GENERATION OF HEAT AT A FRONT-END PORTION OF THE ENDOSCOPE

CROSS-REFERENCE TO RELATED APPLICATION

The present application is a continuation application of PCT/JP2015/082212 filed on Nov. 17, 2015 which is based upon and claims the benefit of priority from Japanese Patent Application No. 2015-022961 filed on Feb. 9, 2015; the entire contents of which are incorporated herein by reference.

BACKGROUND OF THE INVENTION

Field of the Invention

The present invention relates to an endoscope.

Description of the Related Art

An endoscope is an apparatus that has been used widely in a medical field and an industrial field. In the medical field, images of various sites inside a body cavity are achieved by an endoscope inserted into the body cavity. Diagnosis of an observation site is carried out by using these images. Thus, an endoscope has been used for observation and diagnosis of various sites inside the body cavity.

In recent years, as an endoscope for medical treatment, an electronic endoscope has been used in most cases, and an imaging system and an illumination system have been built-in at a front end of an inserting portion that is to be inserted into a body. The imaging system selects image information of a site to be observed which is illuminated, as a video signal, and displays that image on a monitor. The illumination system illuminates a range to be observed.

In the inserting portion, a light guide is accommodated in an internal space running from a front-end portion through a base-end portion. The light guide includes a multiple number of optical fibers in a bundled state. Illuminating light that is incident on one end (incidence end) of the light guide from an external light-source unit is guided to the front-end portion, and emerges from the other end of the light guide (emergence end). The illuminating light from the emergence end is irradiated toward a site to be observed, through an illumination system.

Since an endoscope for medical treatment is to be used inside a body, it is necessary to make an arrangement such that a temperature of an outer surface of the inserting portion does not become high. Among components forming the front-end portion of the endoscope, an image pickup element and the illumination system can be cited as examples of components that contribute to generation of heat at a front-end portion.

With regard to the image pickup element, in recent years, there has been an increase in power consumption due to the large number of pixels and high-speed processing, and an amount of heat generated at the front-end portion due to the rise in temperature has become large. The illumination system, for illuminating an observation range of an object with uniform intensity of illumination, has an illumination lens that spreads a light beam, provided on an emergence-end side of the light guide.

Light emerged from the light guide has an NA (numerical aperture) which is determined according to a material of the light guide. Since the light emerged from the light guide is refracted according to a radius of curvature of the illumination lens, light rays with a large angle, of the light emerged from an outer peripheral portion of the light guide are incident on a side surface (an edge portion) of the illumination lens. In a case in which, the side surface of the illumination lens has been processed to be a grained surface, the light rays are scattered and absorbed at the side surface of the illumination lens. The light rays scattered contribute as energy to the rise in temperature. In a case in which, the side surface of the illumination lens has been processed to be a mirror surface, the light rays being scattered and absorbed at a frame of the lens, contribute similarly to the rise in temperature. When the radius of curvature of the illumination lens is made small for spreading light distribution, since an amount of light falling on the side surface increases, an amount of heat generated increases.

Such an arrangement for reducing the generation of heat at the front-end portion of endoscope is proposed in Japanese Patent Application Laid-open Publication No. 2012-200480 and Japanese Patent Application Laid-open Publication No. 2011-215425. In an arrangement in Japanese Patent Application Laid-open Publication No. 2012-200480, a rod has been used as the illumination lens. Accordingly, a lens diameter of the front-end portion is made large.

Moreover, in an arrangement in Japanese Patent Application Laid-open Publication No. 2011-215425, a lens surface on an emergence side of the illumination lens is let to be a shape having a positive power, or in other words, is let to be a shape having a convex surface directed toward an object side.

In an endoscope with a landscape-oriented aspect ratio of screen, it is necessary to widen the light distribution according to the angle of view of the horizontal direction.

In such manner, an arrangement for illuminating appropriately a landscape-oriented area has been proposed in Japanese Patent Application Laid-open Publication No. Hei 11-326786 and Japanese Patent Application Laid-open Publication No. Hei 8-254659.

SUMMARY OF THE INVENTION

The present invention has been made in view of such problematic points, and an object of the present invention is to provide an endoscope in which, the generation of heat at a front-end portion is reduced.

An endoscope includes
an imaging system; and
an illumination system, wherein
the illumination system includes a light guide and at least one illumination lens, and
the imaging system includes an objective lens unit and an image pickup element, and
when a direction along a long side of the image pickup element is let to be a first direction, and
a direction along a short side of the image pickup element is let to be a second direction,
the illumination system is disposed at a position shifted in the second direction with respect to the imaging system, and
the endoscope satisfies the following conditional expressions (1), (2) and (3)

$$1.35 < A \qquad (1)$$

$$1 < L_H/L_V \qquad (2)$$

$$1.5 < (r_V - L_V)/(r_H - L_H) \leq 3.17 \qquad (3)$$

where,

A denotes a value calculated by the following expression when an aspect ratio long side:short side of an area of the image pickup element corresponding to a display image range is let to be H:V $$A=H/V,$$

$L_H$ denotes a dimension corresponding to the first direction of an end surface on an illumination lens side of the light guide, $L_V$ denotes a dimension corresponding to the second direction of the end surface on the illumination lens side of the light guide, $r_H$ denotes an outer-diameter dimension corresponding to the first direction of the illumination lens, and $r_V$ denotes an outer-diameter dimension corresponding to the second direction of the illumination lens.

BRIEF DESCRIPTION OF THE DRAWINGS

Each of FIG. 3A, FIG. 3B, FIG. 3C, FIG. 3D.

Each of FIG. 4A, FIG. 4B, FIG. 4C.

Each of FIG. 5A, FIG. 5B, FIG. 5C, FIG. 5D.

Each of FIG. 6A, FIG. 6B, FIG. 6C, FIG. 6D.

Each of FIG. 7A

DETAILED DESCRIPTION OF THE INVENTION

Reasons for and effects of adopting such arrangement for an endoscope according to embodiments of the present invention will be described below by using the accompanying diagrams. However, the present invention is not restricted to the embodiments described below.

An endoscope according to an aspect of the present invention has an imaging system, and an illumination system, wherein the illumination system has a light guide and least one illumination lens, and the imaging system has an objective lens unit and an image pickup element, and when a direction along a long side of the image pickup element is let to be a first direction, and a direction along a short side of the image pickup element is let to be a second direction, the illumination system is disposed at a position shifted in the second direction with respect to the imaging system, and the endoscope satisfies the following conditional expressions (1) and (2)

$$1.35<A \tag{1}$$

$$1<L_H/L_V \tag{2}$$

where,

A denotes a value calculated by the following expression when an aspect ratio long side:short side of an area of the image pickup element corresponding to a display image range is let to be H:V $$A=H/V,$$

$L_H$ denotes a dimension corresponding to the first direction of an end surface on an illumination lens side of the light guide, and $L_V$ denotes a dimension corresponding to the second direction of the end surface on the illumination lens side of the light guide.

Conditional expression (1) regulates an appropriate aspect ratio of the area of the image pickup element corresponding to the display image range.

An image picked up by the image pickup element is displayed on an image display unit via an image processing section. The image displayed on the image display unit is referred to as a 'display image'.

The 'aspect ratio of the area of the image pickup element corresponding to the display image range' refers to the value calculated by A=H/V when the ratio of the long side:short side is let to be H:V. More specifically, it refers to (1), (2), and (3) below.

(1) In a case of displaying as it is, an image achieved from an effective image pickup area of the image pickup element, on the image display unit, it is called as an 'aspect ratio of the effective image pickup area'.

(2) In a case of selecting a rectangular-shaped image electrically from the effective image pickup area of the image pickup element, when an image from the area selected is to be displayed on the image display unit, it is called an 'aspect ratio of the image area selected'.

(3) In a case of limiting a light receiving area by disposing a mask member having an opening portion, in the effective image pickup area of the image pickup element, when an image from the area limited is to be displayed on the image display unit, it is called as an 'aspect ratio of the area limited'.

By satisfying conditional expression (1), an observer can view a screen displayed on an entire area or a wide area close to that of a screen of a monitor.

With regard to specification values of each embodiment that will be described later, values of H and V are mentioned as parameters limiting the 'screen aspect ratio'. In specification values and diagrams from FIG. 3 to FIG. 8 of embodiments from a first embodiment to a sixth embodiment, reference numerals H and V indicate relative values (unit: nil) of an area of the image pickup element corresponding to the display image range in the first direction (long-side direction) and the second direction (short-side direction) respectively.

Conditional expression (2) regulates an appropriate shape of an end surface toward the illumination lens of the light guide. By satisfying conditional expression (2), in a cross-sectional shape perpendicular to a central axis of the light guide, a dimension of the light guide becomes smaller in the second direction (short-side direction) as compared to a dimension in the first direction (long-side direction). Consequently, a light ray is not incident on the side surface of the illumination lens in the second direction (short-side direction). As a result of this, it is possible not to let the light to be incident, or to reduce an amount of light incident on the side surface in an approximately $\frac{2}{3}^{rd}$ portion of an outer peripheral portion of the illumination lens for example, including the second direction (short-side direction) of the light guide. Therefore, it is possible to reduce the generation of heat at the front-end portion of the endoscope.

Moreover, it is desirable that the illumination system is disposed at the position shifted in the second direction with respect to the imaging system.

More preferably, it is desirable that a position of the illumination lens of the illumination system is shifted in the second direction with respect to a position of the objective lens unit of the imaging system.

In other words, when the endoscope is viewed from a front-end direction, if the number of illumination systems is one set, the illumination system is disposed at one of the positions in the second direction with respect to the imaging system. Moreover, in a case in which the number of illumination systems is two sets, it is desirable that the illumination system is disposed only at any one of a first position with respect to the imaging system and a second position on an opposite side with respect to the imaging system, of the first position in the second direction, or that the illumination system is disposed at both of the first position and the second position.

The front-end portion of the endoscope generally includes a frame made of a material such as a metal. The illumination system being disposed in the second direction which is a direction along the short-side direction of the image display range, with respect to the imaging system, a thickness of the frame in the second direction with respect to the illumination system becomes thin. In the present aspect, it is possible to make small the generation of heat in the second direction which is the short-side direction with respect to the screen of the imaging system. Consequently, in the second direction, an amount of heat generated being small even when the frame is thin, the temperature is not susceptible to rise, and as a result, it is possible to reduce the rise in temperature of an outer surface of the endoscope.

Moreover, in endoscopes, an organ is to be disposed at a lower side of the screen and to be observed from an upper inclined side in many cases. By disposing the illumination system at the upper side of the screen, at the first position for example, with respect to the imaging system, the illumination system is susceptible to be away from an object. Accordingly, inadequacy of brightness due to halation and dimming is not susceptible to occur.

Moreover, according to a preferable aspect of the present invention, it is desirable to satisfy the following conditional expression (3).

$$1.5 < (r_V - L_V)/(r_H - L_H) \quad (3)$$

where, $L_H$ denotes the dimension corresponding to the first direction of the end surface on the illumination lens side of the light guide, $L_V$ denotes the dimension corresponding to the second direction of the end surface on the illumination lens side of the light guide, $r_H$ denotes an outer-diameter dimension corresponding to the first direction of the illumination lens, and $r_V$ denotes an outer-diameter dimension corresponding to the second direction of the illumination lens.

Conditional expression (3) regulates an appropriate ratio of a difference in an outer-diameter dimension of the illumination lens and a cross-sectional dimension of the light guide in the first direction and a difference in an outer-diameter dimension of the illumination lens and a cross-sectional dimension of the light guide in the second direction. When the endoscope satisfies conditional expression (3), it is possible to reduce the light incident on the side surface of the illumination lens and to reduce effectively the amount of heat generated.

When the illumination lens includes a plurality of lenses, an outer dimension of the illumination lens signifies an outer dimension of a lens nearest to object (object to be observed).

Moreover, according to a preferable aspect of the present invention, it is desirable to satisfy the following conditional expression (4).

$$1 < L_H/L_V < 1.5 \quad (4)$$

where, $L_H$ denotes the dimension corresponding to the first direction of the end surface on the illumination lens side of the light guide, and LV denotes the dimension corresponding to the second direction of the end surface on the illumination lens side of the light guide.

Light rays emerged from a peripheral portion of the light guide are directed toward an outer peripheral side of the light guide and toward a central direction of the light guide. The light rays directed toward the central direction of the light guide are refracted by the illumination lens and illuminate a vicinity of a center of the screen. Therefore, when the dimension in the second direction is excessively small, an amount of light at a central portion decreases and the overall brightness is degraded. When an upper limit value of conditional expression (4) is exceeded, the degradation of the amount of light at the center becomes remarkable, and since the overall brightness is degraded, an observation performance is degraded.

(Description of Overall System)

Figure 1:
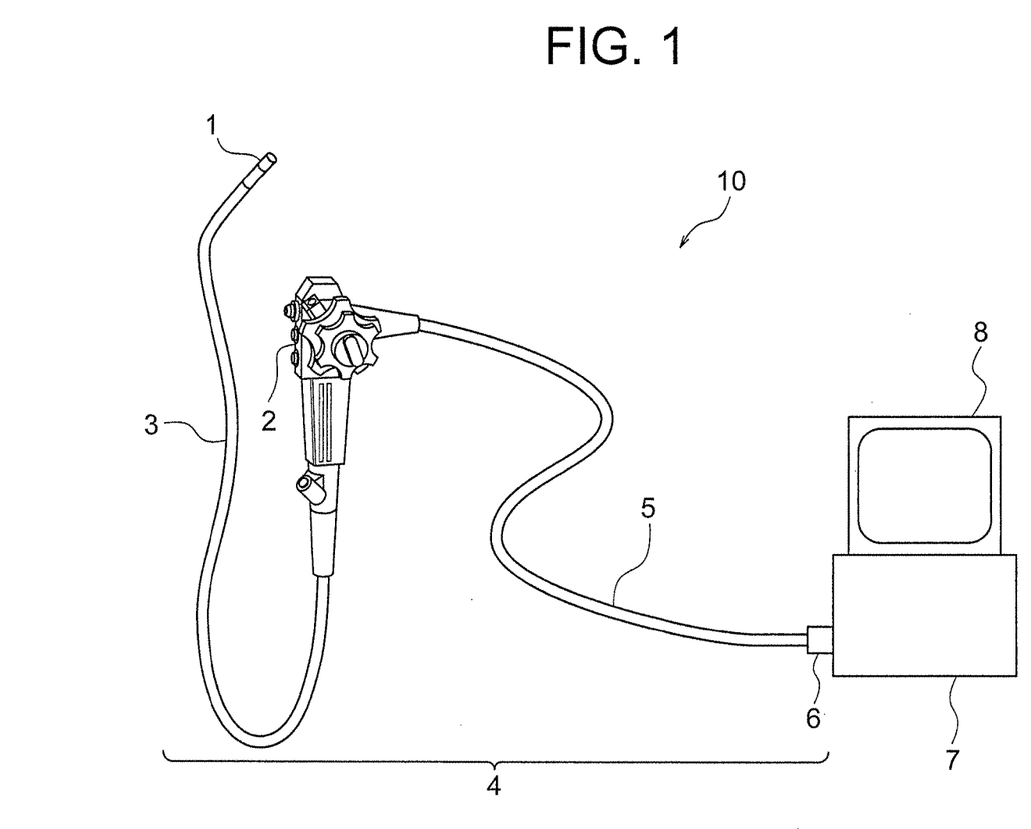
FIG. 1 is a diagram showing a schematic arrangement of an endoscope system having an endoscope according to an embodiment of the present invention.

FIG. 1 is a diagram showing a schematic arrangement of an electronic endoscope system 10 having the endoscope according to the embodiment of the present invention. The electronic endoscope system 10 includes an electronic endoscope 4 and an apparatus outside the body 7. The electronic endoscope 4 includes an inserting portion 3, an operating unit 2, a connecting cord portion 5, and a connector portion 6. Moreover, the apparatus outside the body 7 has a video processor (not shown in the diagram) which carries out processing of a video signal from the electronic endoscope 4 and a display unit 8 which displays on a monitor a video signal from the video processor.

The inserting portion 3 includes a long and slender member having flexibility that can be inserted into a body cavity of a patient, and a front end is a front-end hard portion 1 which is hard. A user (not shown in the diagram) can carry out various operations by an angle knob etc. provided to the operating unit 2.

Moreover, the connecting cord portion 5 is extended from the operating unit 2. The connecting cord portion 5 is connected to the apparatus outside the body 7 via the connector portion 6.

Moreover, the connecting cord portion 5 communicates a power-supply voltage signal from a power-supply unit and the video processor, and a drive signal from the image pickup element to an image pickup system which is built-in in the front-end hard portion 1, and also communicates a video signal from an imaging system to the video processor.

The video processor of the apparatus outside the body 7 is connectible to peripheral equipment such as a video printer and a recording apparatus not shown in the diagram. The video processor carries out a predetermined signal processing on the video signal from the imaging system, and is capable of displaying an endoscope image on a display screen (monitor) of the display unit 8.

The electronic endoscope 4 of the present embodiment is not limited to an arrangement in which the inserting portion 3 is flexible. The inserting portion 3 may be a hard endoscope which does not bend.

First Embodiment

Figure 2:
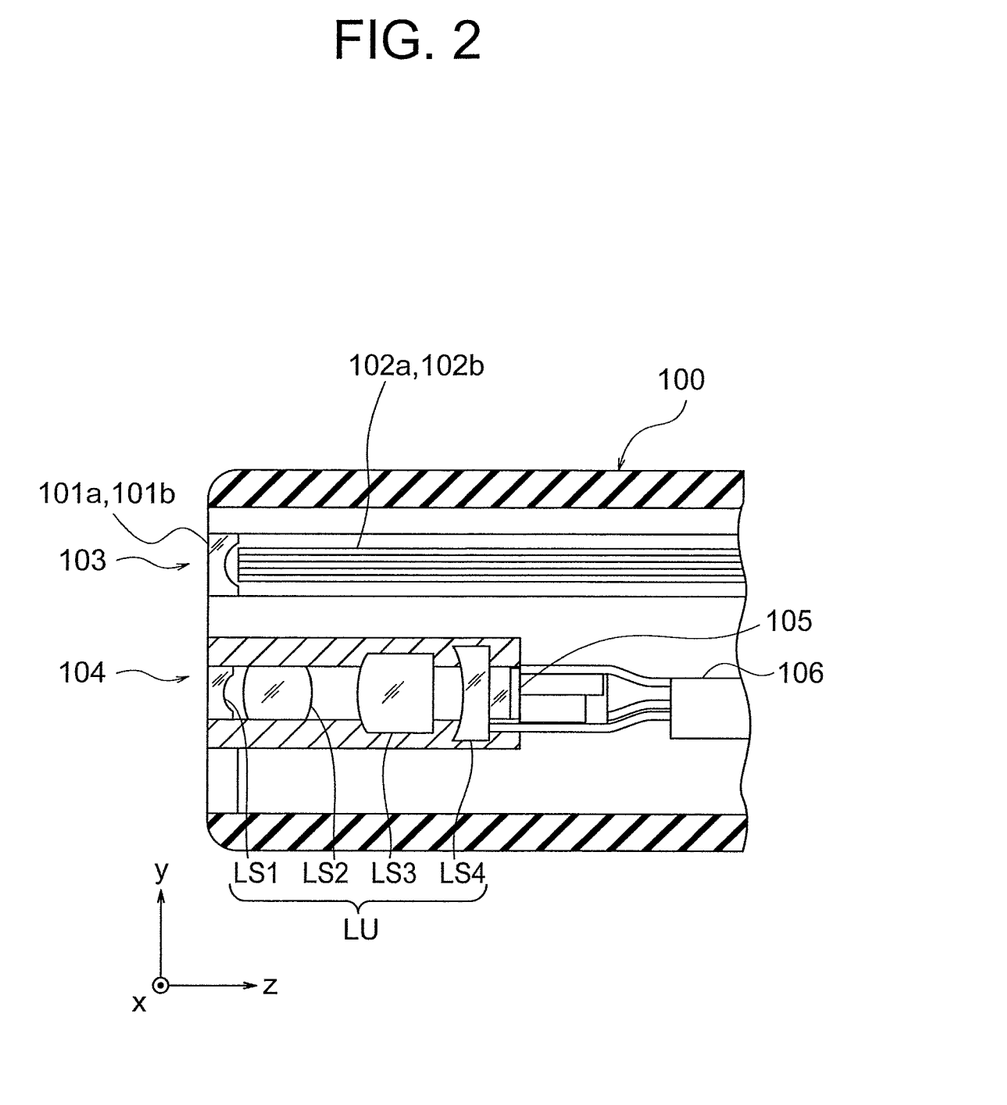
FIG. 2 is a cross-sectional view showing an arrangement of a front-end portion of an endoscope according to a first embodiment of the present invention.

FIG. 2 is a cross-sectional view showing an arrangement in a direction (z-direction) along an optical axis of a front-end portion of an endoscope 100 according to a first embodiment. The present embodiment is a preferred example of a hard endoscope.

The endoscope 100 has an imaging system 104 and an illumination system 103.

The present embodiment has two sets of the illumination system 103. A first illumination system has a light guide 102a and one illumination lens 101a. A second illumination system has a light guide 102b and one illumination lens 101b. The imaging system 104 has an objective lens unit LU and an image pickup element 105. The objective lens unit LU has four lenses LS1, LS2, LS3, and LS4.

The image pickup element 105 is a CCD (charge coupled device) for example. A signal that drives the image pickup element and a signal that is output from the image pickup element are input and output by a signal cable 106.

Figure 3A:
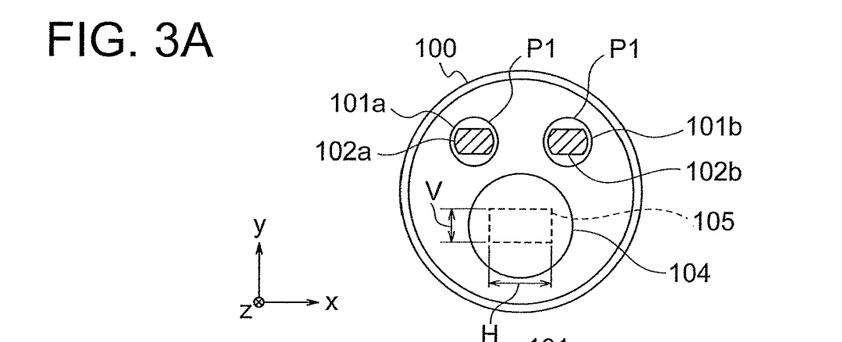
Figure 3B:
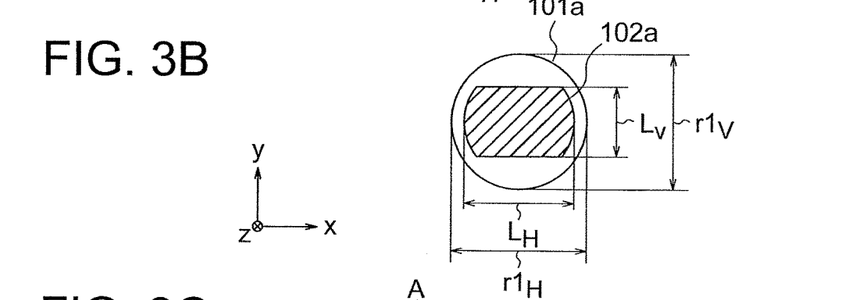
Figure 3C:
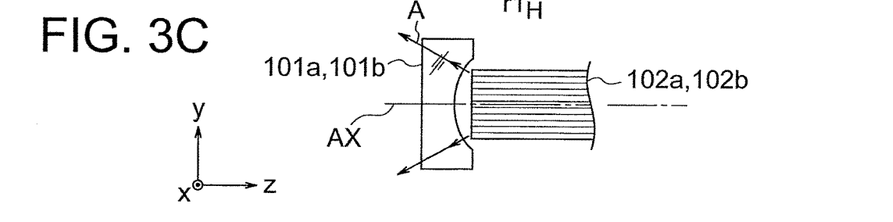
Figure 3D:
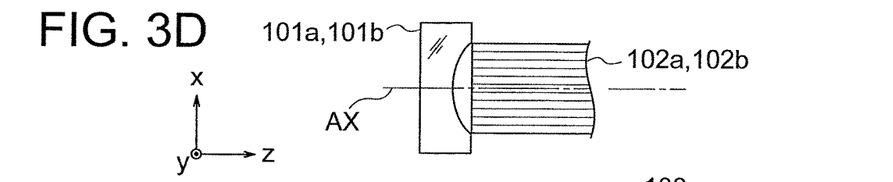

FIG. 3A shows an arrangement of the endoscope 100 viewed from the front-end direction (z-direction). FIG. 3B shows an arrangement of the light guide 102a and the illumination lens 101a viewed from the front-end direction (z-direction). FIG. 3C and FIG. 3D show a cross-sectional view of an arrangement in two different directions respectively, along a central axis AX of the light guide 102a and the illumination lens 101a.

The endoscope 100 satisfies the following conditional expressions (1) and (2).

Here, a direction along a long side of the image pickup element 105 is let to be a first direction, and a direction along a short side of the image pickup element 105 is let to be a second direction.

$$1.35 < A \quad (1)$$

$$1 < L_H/L_V \quad (2)$$

where,

A denotes a value calculated by the following expression when an aspect ratio long side:short side of an area of the image pickup element corresponding to a display image range is let to be H:V $$A = H/V,$$

$L_H$ denotes a dimension corresponding to the first direction (x-direction) of an end surface toward an illumination lens 101a (101b) of the light guide 102a (102b), and $L_V$ denotes a dimension corresponding to the second direction of the end surface toward the illumination lens 101a (101b) of the light guide 102a (102b).

As shown in FIG. 3A, an area of the image pickup element 105 corresponding to a display image range has a rectangular shape. Moreover, an aspect ratio of the area of the image pickup element 105 corresponding to the display image range satisfies conditional expression (1). Accordingly, it is possible to carry out imaging of a landscape-orientation equivalent to an aspect ratio of a screen of a monitor which is the display unit (FIG. 1).

As shown in FIG. 3B, the light guide 102a and the light guide 102b satisfy conditional expression (2). A shape of end surfaces of the light guide 102a and the light guide 102b toward the illumination lens 101a and the illumination lens 101b respectively becomes an oblong shape.

Figure 3E:
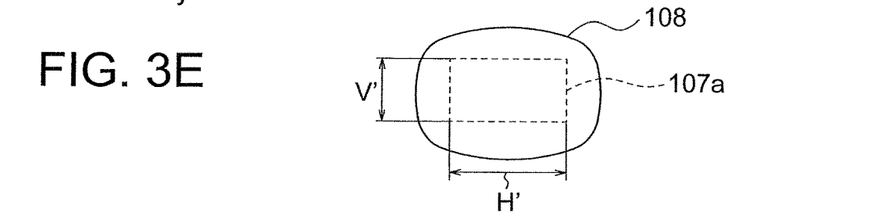
FIG. 3E is a diagram illustrating the endoscope according to the first embodiment of the present invention.

FIG. 3E indicates an observation area 107a and a range to be illuminated (range of light distribution characteristics) 108. By satisfying conditional expressions (1) and (2), it is possible to achieve the range (range of light distribution characteristics) illuminated having an oblong (horizontally long) shape with respect to the observation area 107a which is rectangular with oblong shape. Moreover, dimensions H' and V' of the observation area 107a are substantially proportional to relative dimensions H and V of the area of the image pickup element 105.

Here, as shown in FIG. 3C, light A emerged from the light guide 102a (102b) in the second direction (y-direction) does not hit a side surface or in other words, an edge portion of the illumination lens 101a (101b). Consequently, it is possible to reduce a generation of heat energy at the side surface of the illumination lens, and to prevent the rise in temperature.

The endoscope 100 will be described further by referring to FIG. 3A.

In the present embodiment, the endoscope has two sets of illumination systems namely the first illumination system and the second illumination system.

When the endoscope 100 is viewed from the front-end direction, each of the illumination lens 101a and the illumination lens 101b is disposed at a position P1 shifted in the second direction (y-direction) with respect to the imaging system 104. In other words, the illumination lens 101a and the illumination lens 101b are disposed at any one position P1 only, out of a first position P1 with respect to the imaging system 104 and a second position P2 (not shown in the diagram) on an opposite side of the first position P1, in the second direction (y-direction) with respect to the imaging system 104.

In such manner, in the present embodiment, each of the two illumination lenses 101a and 101b is disposed at only the first position P1. The first position P1 being an upper side of the screen of the imaging system 104, it is possible to illuminate the observation area from the upper side of the screen.

A shape of a cross-section perpendicular to the central axis AX of the light guides 102a and 102b is an oval shape in a circular shape, with two locations of the oval shape in the second direction (y-direction) cut linearly. Moreover, one of the sides cut is facing a peripheral portion of the endoscope 100.

The illumination lenses 101a and 101b are planoconcave lenses of which an outer diameter has a circular shape and an object-side surface is a flat surface. Here, a concave surface has a rotationally symmetrical shape.

As mentioned above, a front-end layout of the endoscope 100 of the present embodiment has two sets of illumination systems disposed at the upper side (in second direction, y-direction) of the screen of the imaging system 104.

Here, as mentioned above, in the cross-section shown in FIG. 3C, the dimension of the light guide in the short-side direction (second direction, y-direction) is smaller as compared to the dimension of the light guide in the long-side direction (first direction, x-direction).

In the cross-section shown in FIG. 3D, light rays hit the side surface of the illumination lens similarly as in the conventional technology.

In the present embodiment, in approximately $\frac{2}{3}^{rd}$ area in the short-side direction (second direction, y-direction), of an outer peripheral portion of the illumination lens, light rays are not incident on the side surface of the illumination lenses 101a and 101b. Or, since an amount of light incident is reduced, it is possible to make small the amount of heat generated at the front end.

A front-end portion of the endoscope includes a metal frame. The illumination lenses being disposed at an upper side of a screen of an imaging system, a thickness of the metal frame at an upper side of an illumination system becomes thin. In the present embodiment, it is possible to make small the amount of heat generated at the upper and lower sides (second direction) of the screen of the illumination system. Therefore, the temperature of the metal frame is not susceptible to increase, and it is possible to reduce the rise in temperature of an outer surface of the endoscope.

Moreover, in endoscopes, an organ to be observed is to be disposed at a lower side of a screen, and to be observed from an upper inclined side in many cases. By disposing the illumination system 103 at an upper side (first position P1) with respect to the imaging system, the illumination system 103 is away from an object in many cases. Accordingly, it is possible to prevent an inadequacy of brightness due to halation and dimming.

Moreover, since the illumination lens 101a and the illumination lens 101b are circular-shaped, workability is favorable. The illumination lens 101a and the illumination lens 101b are made of sapphire. Accordingly, an autoclave (high-temperature and high-humidity sterilization) is possible. In addition, since a curved surface of the illumination lens has a symmetrical spherical shape and an outer diameter thereof has a circular shape, processing of even a hard glass material such as sapphire is possible.

As mentioned above, in the present embodiment, since the amount of heat generated at the upper and the lower side (in second direction, y-direction) of the screen becomes small, it is possible to prevent the rise in temperature of a side surface of the front-end hard portion of the endoscope. Here, although there is a generation of heat at left and right sides (first direction, x-direction) of the screen, the metal frame being thick, since the temperature is not susceptible to be transmitted to an outer side, it does not pose a problem.

Various specification values and values corresponding to conditional expressions for the present embodiment are shown below. Here, the first illumination system includes the illumination lens 101a and the light guide 102a. The second illumination system includes the illumination lens 101b and the light guide 102b. Dimensions in the first direction and the second direction of the illumination lens 101a and the illumination lens 101b being same, are mentioned as an outer-diameter dimension.

| (Unit: mm) | |
|---|---|
| Outer diameter of front end of endoscope | 5.4 |
| Imaging system | |
| Diameter of objective lens | 2.5 |
| Number of pixels of image pickup element | approximately 1 million |
| Aspect ratio of screen | H:V 16:10 |
| Illumination system | |
| Light guide of first illumination system | |
| Dimension in first direction | $L_H$ 0.77 |
| Dimension in second direction | $L_V$ 0.6 |
| Outer-diameter dimension of first illumination lens | $r1_H = r1_V$ 1.1 |
| Material of first illumination lens | sapphire |
| Light guide of second illumination system | |
| Dimension in first direction | $L_H$ 0.77 |
| Dimension in second direction | $L_V$ 0.6 |
| Outer-diameter dimension of second illumination lens | $r2_H = r2_V$ 1.1 |
| Material of second illumination lens | sapphire |
| Layout | |
| Distance between centers of imaging system and first illumination system | 2.2 |
| Distance between centers of imaging system and second illumination system | 2.2 |
| (Values corresponding to conditional expressions) | |
| (1) A | 1.60 |
| (2) First illumination system: | $L_H/L_V$ 1.28 |
| Second illumination system: | $L_H/L_V$ 1.28 |
| (3) First illumination system: | $(r1_V - L_V)/(r1_H - L_H)$ 1.52 |
| Second illumination system: | $(r2_V - L_V)/(r2_H - L_H)$ 1.52 |

Second Embodiment

FIG. 4A, FIG. 4B, FIG. 4C, and FIG. 4D are cross-sectional views showing an arrangement viewed from a direction (z-direction) along an optical axis of a front-end portion of an endoscope 200 according to a second embodiment. The present embodiment is a preferred example of a flexible endoscope. Same reference numerals are assigned to components that are same as in the first embodiment, and repetitive description is omitted.

The endoscope 200 has an imaging system 104 and an illumination system 103 (refer to FIG. 2).

The present embodiment has two sets of the illumination system 103. A first illumination system has a light guide 202a and one illumination lens 201a. A second illumination system has a light guide 202b and one illumination lens 201b. The imaging system 104 has an objective lens unit LU and an image pickup element 105. Moreover, although it is not shown in FIG. 2, a channel for inserting a treatment tool passes through the endoscope from the front-end hard portion 1 up to the operating unit 2.

Figure 4A:
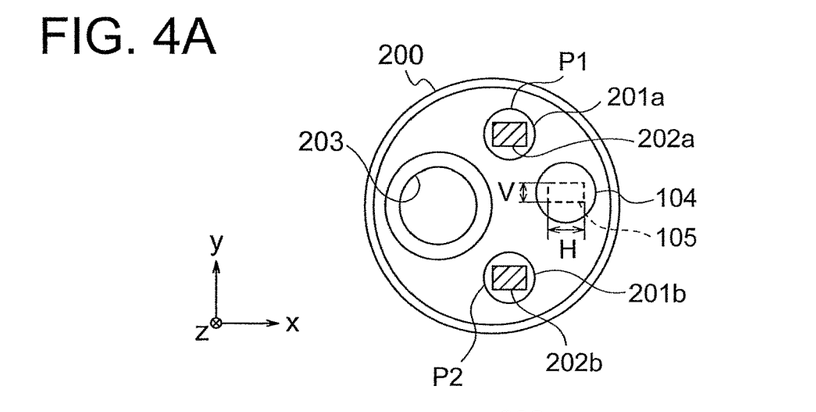
Figure 4B:
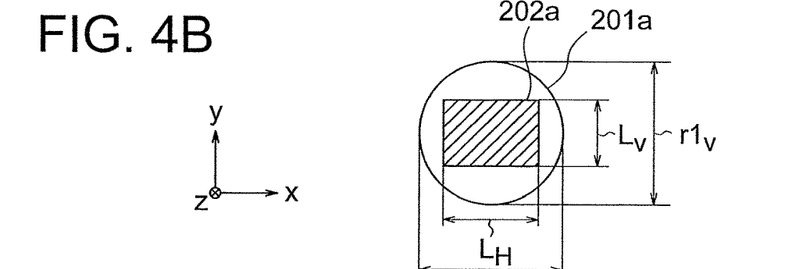
Figure 4C:
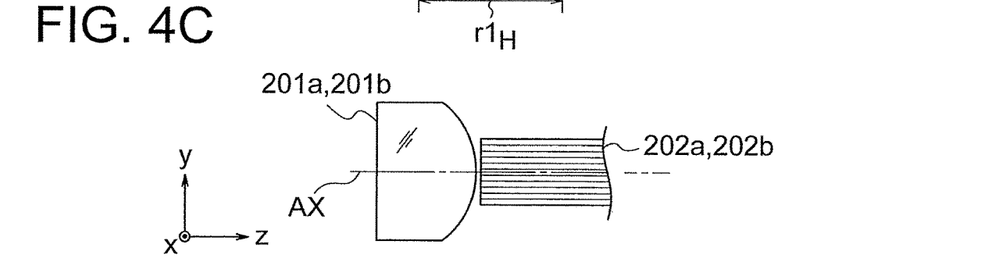
Figure 4D:
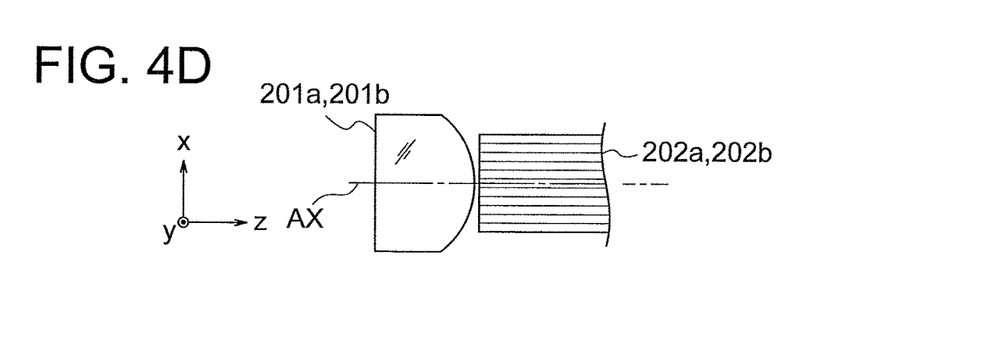
FIG. 4D is a diagram illustrating an endoscope according to a second embodiment of the present invention.

FIG. 4A shows an arrangement of the endoscope 200 viewed from the front-end direction (z-direction). FIG. 4B shows an arrangement of the light guide 202a and the illumination lens 201a viewed from the front-end direction (z-direction). FIG. 4C and FIG. 4D show a cross-sectional view of an arrangement in two different directions respectively along a central axis AX of the light guide 202a and the illumination lens 201a.

As shown in FIG. 4B, the light guide 202a and the light guide 202b satisfy conditional expression (2). Accordingly, a shape of end surfaces of the light guide 202a and the light 202b toward the illumination lens 201a and the illumination lens 201b respectively becomes an oblong rectangular shape.

The endoscope 200 will be described further by referring to FIG. 4A.

In the present embodiment, the endoscope has two sets of illumination systems namely the first illumination system and the second illumination system.

When the endoscope 200 is viewed from the front-end direction, the illumination lens 201a and the illumination lens 201b are disposed at a position shifted in the second direction (y-direction) with respect to the imaging system 104. In other words, the illumination lens 201a and the illumination lens 201b are disposed at both of a first position P1 with respect to the imaging system 104 and a second position P2 (not shown in the diagram) on an opposite side of the first position P1, in the second direction (y-direction) with respect to the imaging system 104.

In the present embodiment, the endoscope has two sets of illumination systems as mentioned above. The illumination lens 201a and the illumination lens 201b are disposed at the first position P1 and the second position P2 respectively. According to this arrangement, at the time of observation, it is possible to illuminate an observation area from an upper side and a lower side of the screen.

A shape of a cross-section perpendicular to the central axis AX of the light guides 202a and 202b is a rectangular shape.

An outer diameter of the illumination lenses 201a and 201b has a circular shape. An object-side surface of the illumination lenses 201a and 201b is a planoconvex lens. Here, a convex surface has a rotationally symmetrical shape.

As mentioned above, a front-end layout of the endoscope 200 of the present embodiment has two sets of illumination systems namely the first illumination system and the second illumination system disposed at the upper side and the lower side (in second direction, y-direction) of the screen of the imaging system 104.

In the cross-section shown in FIG. 4C, a dimension of the light guide in a short-side direction (second direction, y-direction) is smaller as compared to a dimension of the light guide in the long-side direction (first direction, x-direction) Therefore, light rays are not incident on side surfaces of the illumination lens 201a and the illumination lens 201b. As a result, it is possible to reduce an amount of heat generated.

In the cross-section shown in FIG. 4D, light rays hit the side surfaces of the illumination lenses similarly as in the conventional technology.

A front-end portion of the endoscope includes a metal frame. The illumination lenses being disposed at the upper side and the lower side (in second direction, y-direction) of the screen, a thickness of the metal frame at an upper side of the illumination lens 201a and at a lower side of the illumination lens 201b becomes thin. In the present embodiment, it is possible to make small the amount of heat generated at the upper side and the lower side of the screen of the illumination system. Therefore, the temperature of the metal frame is not susceptible to rise, and it is possible to reduce the rise in temperature of an outer surface of the endoscope.

Although there is a generation of heat at a left side and a right side (in first direction, x-direction) of the screen, the metal frame being thick, since the temperature is not susceptible to be transmitted to an outer side, it does not pose a problem.

Various specification values and values corresponding to conditional expressions for the present embodiment are shown below. Here, the first illumination system includes the illumination lens 201a and the light guide 202b. The second illumination system includes the illumination lens 201b and the light guide 202b. Dimensions in the first direction and the second direction of the illumination lens 201a and the illumination lens 201b being same, are mentioned as an outer-diameter dimension.

| (Unit: mm) | |
|---|---|
| Outer diameter of front end of endoscope | 5 |
| Imaging system | |
| Diameter of objective lens | 1.2 |
| Number of pixels of image pickup element | approximately 500,000 |
| Aspect ratio of screen | H:V 16:9 |
| Illumination system | |
| Light guide of first illumination system | |
| Dimension in first direction | $L_H$ 0.8 |
| Dimension in second direction | $L_V$ 0.55 |
| Outer-diameter dimension of first illumination lens | $r1_H = r1_V$ 1.1 |
| Material of first illumination lens | glass Nd = 1.883 |
| Light guide of second illumination system | |
| Dimension in first direction | $L_H$ 0.8 |
| Dimension in second direction | $L_V$ 0.55 |
| Outer-diameter dimension of second illumination lens | $r2_H = r2_V$ 1.1 |
| Material of second illumination lens | glass Nd = 1.883 |
| Layout | |
| Distance between centers of imaging system and first illumination system | 1.7 |
| Distance between centers of imaging system and second illumination system | 2.2 |
| (Values corresponding to conditional expressions) | |
| (1) A | 1.78 |
| (2) First illumination system: | $L_H/L_V$ 1.45 |
| Second illumination system: | $L_H/L_V$ 1.45 |
| (3) First illumination system: | $(r1_V - L_V)/(r1_H - L_H)$ 1.83 |
| Second illumination system: | $(r2_V - L_V)/(r2_H - L_H)$ 1.83 |

Third Embodiment

FIG. 5A, FIG. 5B, FIG. 5C, FIG. 5D, and FIG. 5E are cross-sectional views showing an arrangement viewed from a direction (z-direction) along an optical axis of a front-end portion of an endoscope 300 according to a third embodiment. The present embodiment is a preferred example of a flexible endoscope. Same reference numerals are assigned to components that are same as in the first embodiment, and repetitive description is omitted.

The endoscope 300 has an imaging system 104 and an illumination system 103 (refer to FIG. 2).

Figure 5A:
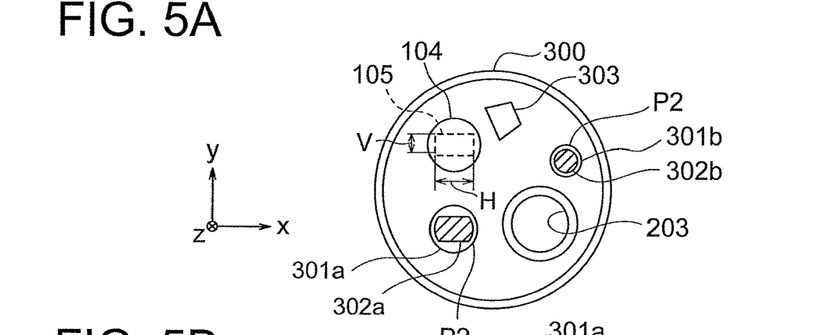

The present embodiment has two sets of the illumination system 103. A first illumination system has a light guide 302a and an illumination lens 301a which includes three lenses. A second illumination system has a light guide 302b and an illumination lens 301b which includes three lenses. An arrangement of the illumination lens 301b including the three lenses is same as an arrangement of the illumination lens 301a, and is omitted to avoid repetition.

The imaging system 104 has an objective lens unit LU (refer to FIG. 2) and an image pickup element 105. Moreover, although it is not shown in FIG. 5A, a channel for inserting a treatment tool passes through the endoscope from the front-end hard portion 1 up to the operating unit 2, and a tube for supplying air and water passes through the endoscope from the front-end hard portion up to the connector portion 6.

Figure 5B:
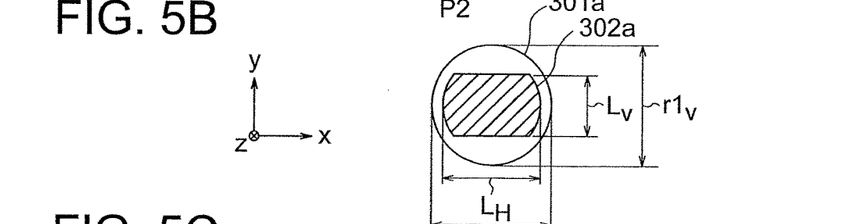

FIG. 5A shows an arrangement of the endoscope 300 viewed from the front-end direction (z-direction). FIG. 5B shows an arrangement of the light guide 302a and the illumination lens 301a viewed from the front-end direction (z-direction). FIG. 5D and FIG. 5E show a cross-sectional view of an arrangement in two different directions respectively, along a central axis AX of the light guide 302a and the illumination lens 301a.

As shown in FIG. 5B, the light guide 302a satisfies conditional expression (2). As shown in the diagram, a shape of an end surface of the light guide 302a toward the illumination lens 301a becomes an oblong shape.

Figure 5C:
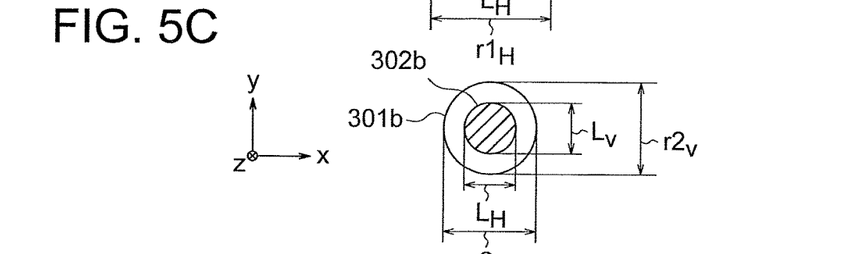
Figure 5D:
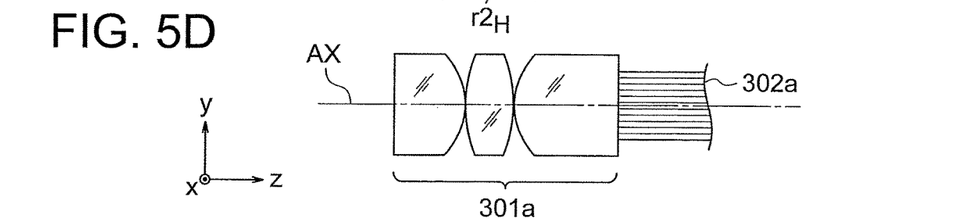
Figure 5E:
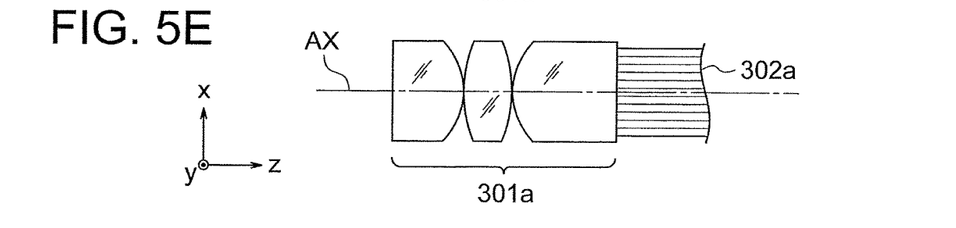
FIG. 5E is a diagram illustrating an endoscope according to a third embodiment of the present invention.

Moreover, as shown in FIG. 5C, a shape of the light guide 302b toward the illumination lens 301b is a circular shape.

The endoscope 300 has a nozzle 303 for supplying air and water.

The endoscope 300 will be described further by referring to FIG. 5A.

In the present embodiment, the endoscope has two sets of illumination systems namely, the first illumination system and the second illumination system.

When the endoscope 300 is viewed from the front-end direction, the illumination lens 301a is disposed at a position P2 shifted in the second direction (y-direction) with respect to the imaging system 104.

A shape of a cross-section perpendicular to the central axis AX of the light guide 302a is an oval shape in a circular shape, with two locations of the oval shape in the second direction (y-direction) cut linearly. One of the sides cut is facing a periphery of the endoscope 300.

An outer diameter of each of the illumination lens 301a and the illumination lens 301b has a circular shape. The illumination lens 301a includes in order from an object side three lenses namely, a planoconvex positive lens, a biconvex positive lens, and a convexoplane positive lens. Here, a convex surface has a rotationally symmetrical shape. The illumination lens 301b also has a lens arrangement same as the lens arrangement of the illumination lens 301a.

As mentioned above, in a front-end layout of the endoscope 300 of the present embodiment, the first illumination system including the light guide 302a is disposed at a lower side of the screen of the imaging system 104, and the second illumination system including the light guide 302b is disposed at an upper side of the screen.

Here, in the cross-section shown in FIG. 5D, a dimension of the light guide 302a in a short-side direction (second direction, y-direction) is smaller as compared to a dimension of the light guide 302a in a long-side direction (first direction, x-direction). Therefore, light rays are not incident on a side surface of the illumination lens 301a. As a result, it is possible to reduce generation of heat in this direction.

In the cross-section shown in FIG. 5E, light rays hit the side surface of the illumination lens similarly as in the conventional technology.

The front-end portion of the endoscope includes a metal frame. The illumination lens 301a being disposed at the lower side of the screen of the imaging system, a thickness of the metal frame at a lower side of the illumination system becomes thin. In the present embodiment, it is possible to make small the amount of heat generated at the upper side and the lower side (in second direction) of the screen of the illumination system. Therefore, the temperature of the metal frame is not susceptible to increase, and it is possible to reduce the rise in temperature of an outer surface of the endoscope.

Although there is a generation of heat at a left side and a right side (in first direction, x-direction) of the screen, the metal frame being thick, since the temperature is not susceptible to be transmitted to an outer side, it does not pose a problem.

In the present embodiment, out of the two sets of illumination systems, only in the first illumination system in which the number of optical fibers in the light guide 302a is large, a dimension in the short-side direction (second direction, y-direction) is let to be smaller as compared to a dimension in the long-side direction (first direction, x-direction) in a cross-section of the light guide 302a.

The light guide 302a having a diameter larger as compared to the diameter of the light guide 302b has a higher influence on heat generation. Therefore, by making the diameter of the light guide 302a oval-shaped, it is possible to reduce the heat generation effectively.

A cross-sectional shape of the light guide 302b with a small number of optical fibers is circular. The diameter of the light guide 302b being small, an amount of heat generated is also small.

Various specification values and values corresponding to conditional expressions for the present embodiment are shown below. Here, the first illumination system includes the illumination lens 301a and the light guide 302a. The second illumination system includes the illumination lens 301b and the light guide 302b. Dimensions in the first direction and the second direction of the illumination lens 301a and the illumination lens 301b being same, are mentioned as an outer-diameter dimension.

| (Unit: mm) | |
|---|---|
| Outer diameter of front end of endoscope | 10 |
| Imaging system | |
| Diameter of objective lens | 2.3 |
| Number of pixels of image pickup element | approximately 500,000 |
| Aspect ratio of screen | H:V 16:9 |
| Illumination system | |
| Light guide of first illumination system | |
| Dimension in first direction | $L_H$ 2 |
| Dimension in second direction | $L_V$ 1.35 |
| Outer-diameter dimension of first illumination lens | $r1_H = r1_V$ 2.3 |
| Material of first illumination lens | glass |
| Light guide of second illumination system | |
| Dimension in first direction | $L_H$ 1.1 |
| Dimension in second direction | $L_V$ 1.1 |
| Outer-diameter dimension of second illumination lens | $r2_H = r2_V$ 1.3 |
| Material of second illumination lens | glass |
| Layout | |
| Distance between imaging system and first illumination system | 4 |
| Distance between imaging system and second illumination system | 4.8 |
| (Values corresponding to conditional expressions) | |
| (1) A | 1.67 |
| (2) First illumination system: | $L_H/L_V$ 1.48 |
| Second illumination system: | $L_H/L_V$ -- |
| (3) First illumination system: | $(r1_V - L_V)/$ 3.17 |
| | $(r1_H - L_H)$ |
| Second illumination system: | $(r2_V - L_V)/$ -- |
| | $(r2_H - L_H)$ |

Here, '--' indicates that conditional expression is not satisfied.

Fourth Embodiment

FIG. 6A, FIG. 6B, FIG. 6C, FIG. 6D, and FIG. 6E are cross-sectional views showing an arrangement viewed from a direction (z-direction) along an optical axis of a front-end portion of an endoscope 400 according to a fourth embodiment. Same reference numerals are assigned to components that are same as in the first embodiment, and repetitive description is omitted.

The endoscope 400 has an imaging system 104 and an illumination system 103 (refer to FIG. 2).

Figure 6A:
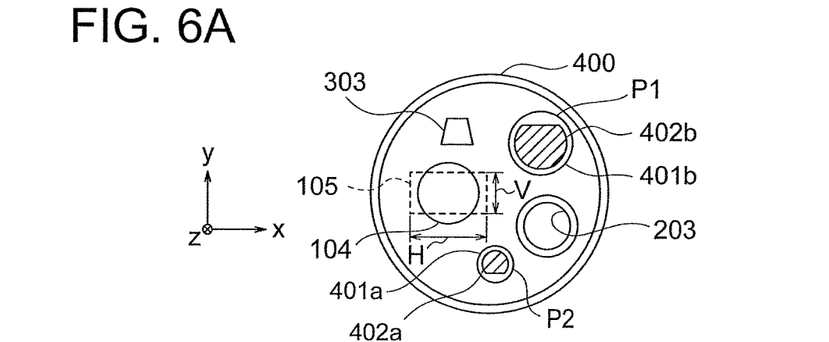

The present embodiment has two sets of the illumination system 103. A first illumination system has a light guide 402a, and an illumination lens 401a which includes three lenses. A second illumination system has a light guide 402b, and an illumination lens 401b which includes three lenses.

Figure 6B:
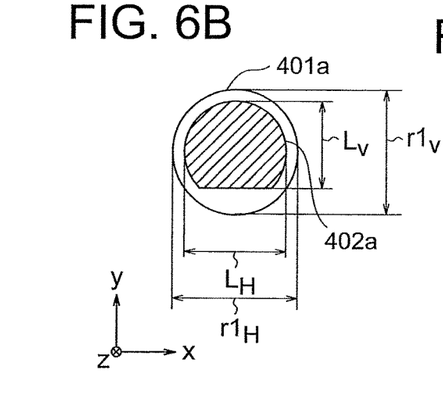
Figure 6C:
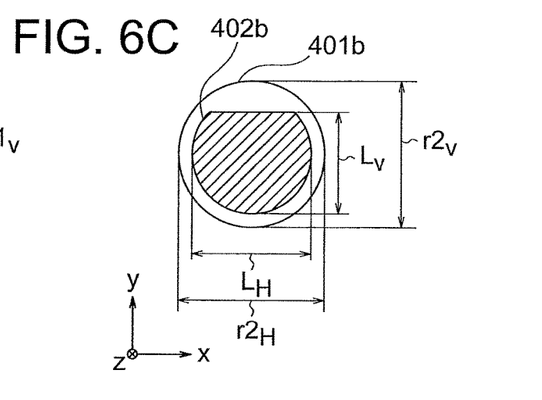
Figure 6D:
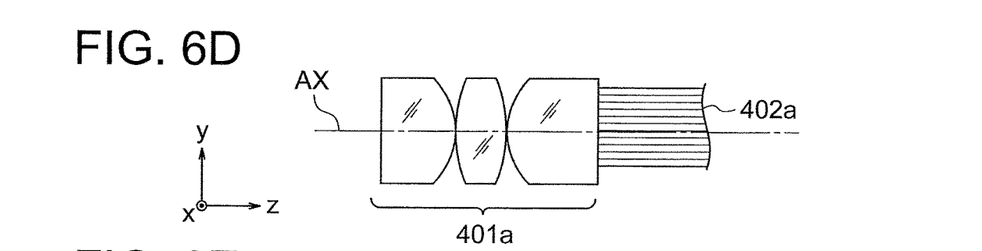
Figure 6E:
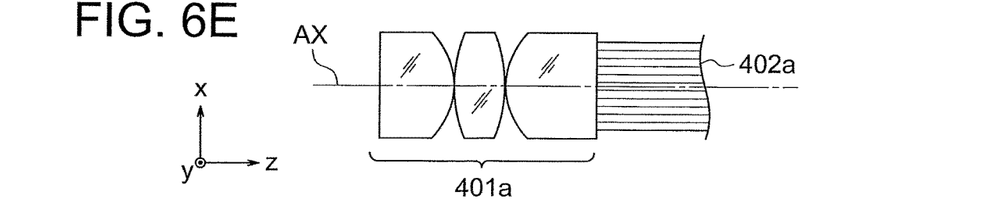
FIG. 6E is a diagram illustrating an endoscope according to a fourth embodiment of the present invention.

FIG. 6A shows an arrangement of the endoscope 400 viewed from the front-end direction (z-direction). FIG. 6B shows an arrangement of the light guide 402a and the illumination lens 401a viewed from the front-end direction (z-direction). FIG. 6C shows an arrangement of the light guide 402b and the illumination lens 401b viewed from the front-end direction (z-direction). FIG. 6D and FIG. 6E show a cross-sectional view of an arrangement in two different directions respectively, along a central axis AX of the light guide 402a and the illumination lens 401a.

As shown in FIG. 6B and FIG. 6C, the light guide 402a and the light guide 402b satisfy conditional expression (2). A shape of end surfaces of the light guide 402a and the light guide 402b toward the illumination lens 401a and the illumination lens 401b respectively is so-called D-cut shape with a part of a circular shape cut out. A direction of cutting is facing a periphery of the endoscope 400.

Moreover, the endoscope 400 of the present embodiment has a nozzle 303 for supplying air and water.

The endoscope 400 will be described further by referring to FIG. 6A.

In the present embodiment, the endoscope has two sets of illumination systems namely, the first illumination system and the second illumination system.

When the endoscope is viewed from a front-end direction, the illumination lens 401a and the illumination lens 401b are disposed at positions P2 and P1 respectively, shifted in a second direction (y-direction) with respect to the imaging system 104. In other words, the illumination lens 401a and the illumination lens 401b are disposed at both of a first position P1 (not shown in the diagram) with respect to the imaging system 104, and a second position P2 (not shown in the diagram) on an opposite side of the first position P1, in the second direction (y-direction) with respect to the imaging system 104.

A shape of a cross-section perpendicular to the central axis AX of the light guide 402a is a D-cut shape in a circular shape, with a lower side of the second direction (y-direction) with respect to the screen of the imaging system, cut linearly.

A shape of a cross-section perpendicular to the central axis AX of the light guide 402b is a D-cut shape in a circular shape, with an upper side of the second direction (y-direction) with respect to the screen of the imaging system, cut linearly.

In such manner, in the present embodiment, a dimension of only a portion of the light guide near an outer surface of the endoscope 400 is to be made small, or in other words, to be made D-cut. Consequently, since it is possible to make small the degradation in an amount of overall light while reducing the heat generation, an arrangement is advantageous for brightness.

An outer diameter of each of the illumination lens 401a and the illumination lens 401b has a circular shape. For instance, the illumination lens 401a includes in order from an object side, three lenses namely, a planoconvex positive lens, a biconvex positive lens, and a convexoplane positive lens. Here, a convex surface has a rotationally symmetrical shape. The illumination lens 401b also has a lens arrangement same as the lens arrangement of the illumination lens 401a.

As mentioned above, in a front-end layout of the endoscope 400 of the present embodiment, two sets of illumination systems are disposed at an upper side and a lower side (in second direction, y-direction) of the screen of the imaging system 104.

Here, in the cross-section shown in FIG. 6D, a dimension of the light guide 402a in a short-side direction (second direction, y-direction) is smaller as compared to a dimension of the light guide 402a in a long-side direction (first direction, x-direction). Therefore, light rays are not incident on a lower side of FIG. 6D, of a side surface of the illumination lens 401a. As a result, it is possible to reduce an amount of heat generated.

On the upper side of FIG. 6D and in the cross-section shown in FIG. 6E, light rays hit the side surface of the illumination lens 401a similarly as in the conventional technology.

The front-end portion of the endoscope includes a metal frame. The illumination lens 401a being disposed at the upper side and the lower side of the screen of the imaging system of the imaging system, a thickness of the metal frame at an upper side of the illumination lens 401a and at a lower side of the illumination lens 401b becomes thin. In the imaging system of the present embodiment, it is possible to make small the amount of heat generated at the lower side of the illumination lens 401a and at the upper side (in second direction) of the illumination lens 401b, letting the screen as a reference. Therefore, the temperature of the metal frame is not susceptible to increase, and it is possible to reduce the rise in temperature of an outer surface of the endoscope.

Although there is a generation of heat in side surface of lens at the left side and the right side (in first direction, x-direction) of the screen and on a side where the light guide is not D-cut, the metal frame being thick, since temperature is not susceptible to be transmitted to an outer side, it does not pose a problem.

(Other Arrangements)

The cross-section of the light guides 402a and 402b may have any shape such as a rectangular shape, a circular shape with an upper side and a lower side of the circle cut or a circular shape with one of the upper side and the lower side of the circle cut, an oblong elliptical shape, and an oblong polygonal shape.

Moreover, in this case, an outer-diameter shape of the illumination lens can also be let to be an elliptical shape or a rectangular shape according to the layout of cross-section of the endoscope 400.

Various specification values and values corresponding to conditional expressions for the present embodiment are shown below. Here, the first illumination system includes the illumination lens 401a and the light guide 402a. The second illumination system includes the illumination lens 401b and the light guide 402b. Dimensions in the first direction and the second direction of the illumination lens 401a and the illumination lens 401b being same, are mentioned as an outer-diameter dimension.

| (Unit: mm) | |
| --- | --- |
| Outer diameter of front end of endoscope | 9.8 |
| Imaging system | |
| Diameter of objective lens | 2.8 |
| Number of pixels of image pickup element | approximately 1 million |
| Aspect ratio of screen | H:V 16:9 |
| Illumination system | |
| Light guide of first illumination system | |
| Dimension in first direction | $L_H$ 1.4 |
| Dimension in second direction | $L_V$ 1.1 |
| Outer-diameter dimension of first illumination lens | $r1_H = r1_V$ 1.7 |
| Material of first illumination lens | glass |
| Light guide of second illumination system | |
| Dimension in first direction | $L_H$ 2.5 |
| Dimension in second direction | $L_V$ 2.1 |
| Outer-diameter dimension of second illumination lens | $r2_H = r2_V$ 2.8 |
| Material of second illumination lens | glass |
| Layout | |
| Distance between imaging system and first illumination system | 3.7 |
| Distance between imaging system and second illumination system | 4.3 |
| (Values corresponding to conditional expressions) | |
| (1) A | 1.78 |
| (2) First illumination system: | $L_H/L_V$ 1.27 |
| Second illumination system: | $L_H/L_V$ 1.19 |
| (3) First illumination system: | $(r1_V - L_V)/(r1_H - L_H)$ 2.00 |
| Second illumination system: | $(r2_V - L_V)/(r2_H - L_H)$ 2.33 |

Fifth Embodiment

Figure 7A:
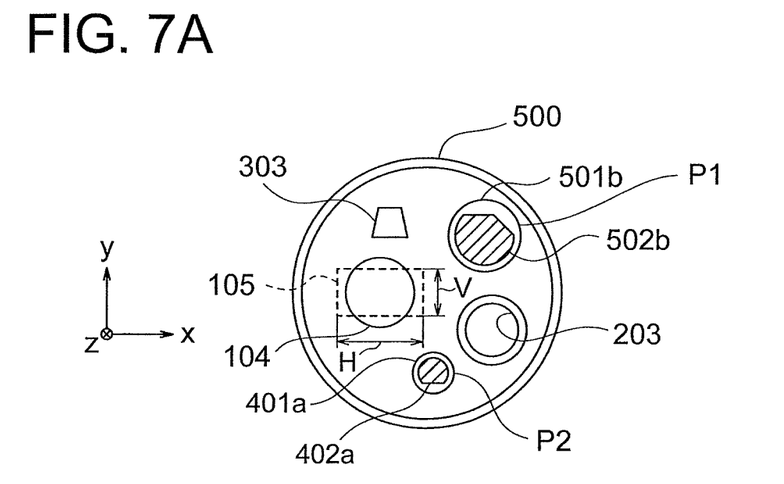
Figure 7B:
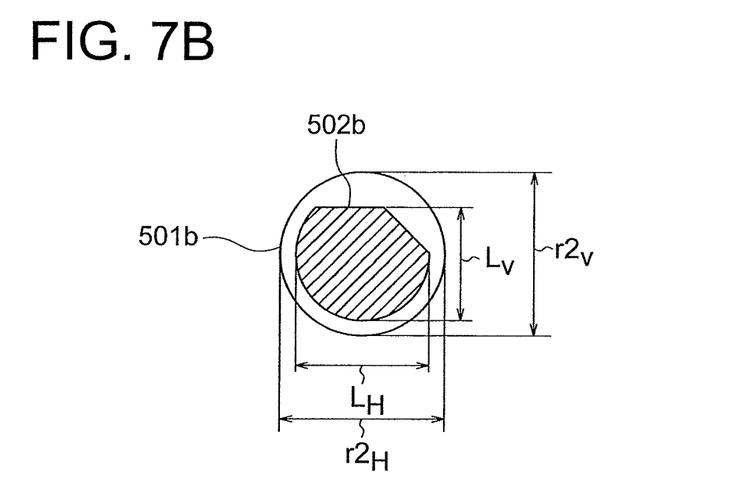
FIG. 7B is a diagram illustrating an endoscope according to a fifth embodiment of the present invention; and Each of FIG. 8A, FIG. 8B, FIG. 8C.

FIG. 7A and FIG. 7B are cross-sectional views showing an arrangement viewed from a direction (z-direction) along an optical axis of a front-end portion of an endoscope 500 according to a fifth embodiment. The endoscope 500 is a preferred example of a flexible endoscope. Same reference numerals are assigned to components that are same as in the fourth embodiment, and repetitive description is omitted.

A portion of a light guide 502b, facing an outer peripheral direction of the front end of the endoscope 500 is cut at an angle at two locations. FIG. 7B shows a cross-sectional shape of an end surface of the light guide 502b. The endoscope 500 has the same arrangement as the endoscope 400 of the fourth embodiment except for a point that a shape of the light guide 502b is different.

In the present embodiment, the portion of the light guide 502b facing the outer peripheral direction of the front end of the endoscope 500 is cut at an angle. Consequently, an amount of heat generated in an outer-diameter direction becomes small, and it is possible to reduce further the rise in temperature of the front-end portion of the endoscope 500.

An upper side (in second direction, y-direction) of the screen of the light guide 402a of the first illumination system has not been cut. Therefore, the upper side (in second direction, y-direction) of the screen is illuminated by illumination light from the light guide 402a. Consequently, as light distribution characteristics of the present embodiment, desirable characteristics are achieved without any problem at the time of observation by the endoscope.

Various specification values are shown below. Numerical values overlapping with the fourth embodiment are omitted. Here, a second illumination system includes the illumination lens 501b and the light guide 502b. Dimensions in the first direction and the second direction of the illumination lens 501b being same, are mentioned as an outer-diameter dimension.

| (Unit: mm) | |
| --- | --- |
| Illumination system | |
| Light guide of second illumination system | |
| Dimension in first direction | $L_H$ 2.5 |
| Dimension in second direction | $L_V$ 2.1 |
| Diameter of second illumination lens | $r2_H = r2_V$ 2.8 |
| Material of second illumination lens | glass |

Sixth Embodiment

FIG. 8A, FIG. 8B, FIG. 8C, and FIG. 8D are cross-sectional views showing an arrangement viewed from a direction (z-direction) along an optical axis of a front-end portion of an endoscope 600 according to a sixth embodiment. The endoscope 600 is a preferred example of a flexible endoscope. Same reference numerals are assigned to components that are same as in the abovementioned embodiments, and repetitive description is omitted.

The endoscope 600 has an imaging system 104 and an illumination system 103 (FIG. 2).

Figure 8A:
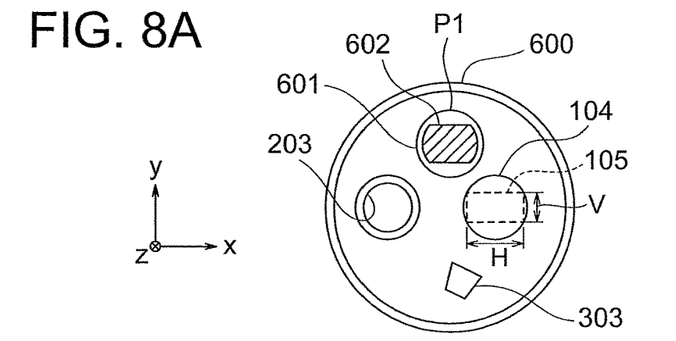
Figure 8B:
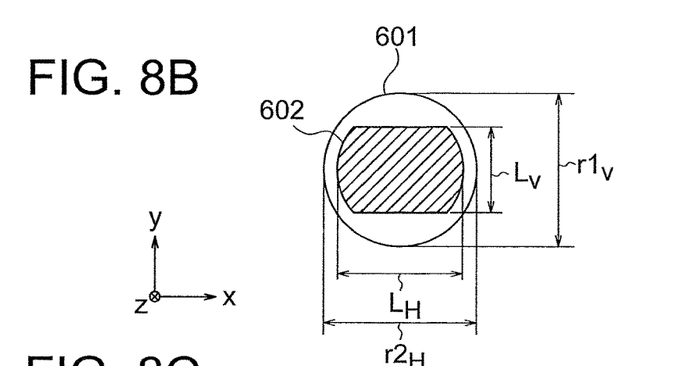
Figure 8C:
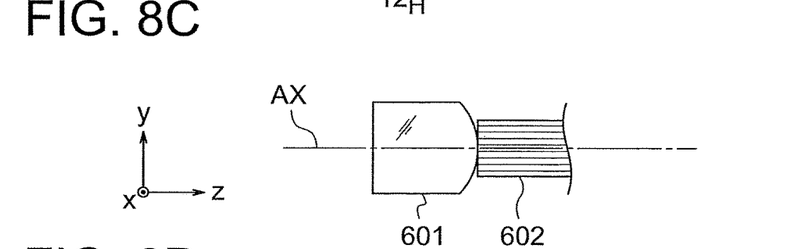
Figure 8D:
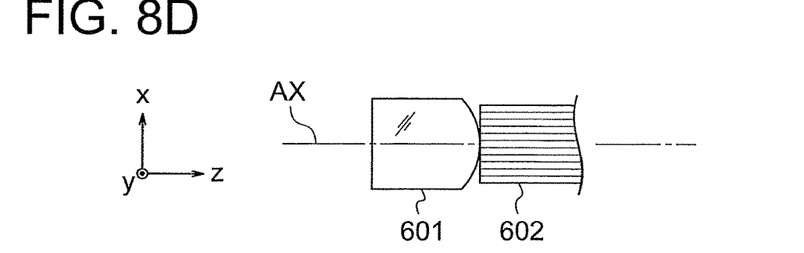
FIG. 8D is a diagram illustrating an endoscope according to a sixth embodiment of the present invention.

The present embodiment has one set of illumination system 103. The one set of illumination system has a light guide 602 and one illumination lens 601.

A shape of a cross-section perpendicular to a central axis AX of the light guide 602 is an oval shape in a circular shape, with two locations of the oval shape in the second direction (y-direction) cut linearly. Moreover, one of the directions of cutting is facing a circumferential portion of the endoscope 600.

An outer diameter of the illumination lens 601 has a circular shape, and an object-side surface thereof is a plano-convex lens of which an object-side surface is a flat surface. Here, a convex surface has a rotationally symmetrical shape.

In the present embodiment, a portion of the light guide 601 facing an outer circumferential direction of a front end of the endoscope 600 is cut linearly. Therefore, an amount of heat generated in an outer circumferential direction becomes small, and it is possible to reduce a rise in temperature of the front-end portion of the endoscope 600. Moreover, although there is a generation of heat at a left side and a right side (in first direction, x-direction) the metal frame being thick, since the temperature is not susceptible to be transmitted to an outer side of the scope, it does not pose a problem.

Various specification values and values corresponding to conditional expressions for the present embodiment are shown below. Dimensions in the first direction and the second direction of the illumination lens 601 being same, are mentioned as an outer-diameter dimension.

| (Unit: mm) | |
|---|---|
| Outer diameter of front end of endoscope | 5.2 |
| Imaging system | |
| Diameter of objective lens | 1.3 |
| Number of pixels of image pickup element | approximately 500,000 |
| Aspect ratio of screen | H:V 1.36:1 |
| Illumination system | |
| Light guide of illumination system | |
| Dimension in first direction | $L_H$ 0.9 |
| Dimension in second direction | $L_V$ 0.8 |
| Outer-diameter dimension of first illumination lens | $r1_H = r1_V$ 1 |
| Material of first illumination lens | glass |
| Layout | |
| Distance between centers of imaging system and illumination system | 1.7 |
| (Values corresponding to conditional expressions) | | |
| (1) | A | 1.36 |
| (2) | Illumination system: | $L_H/L_V$ 1.13 |
| (3) | Illumination system: | $(r1_V - L_V)/$ 2.00 $(r1_H - L_H)$ |

In each of the embodiments, the number of illumination systems is one set or two sets. However, without restricting to this, the number of illumination systems may be three or more than three.

Various embodiments of the present invention have been described above. However, the present invention is not limited to these embodiments, and embodiments in which arrangements of these embodiments are combined without departing from the scope of the present invention, also fall under the category of the present invention.

As described above, the present invention is useful for an endoscope in which a heat generation at a front-end portion is reduced.

According to the present invention, an effect is shown that it is possible to provide an endoscope in which the generation of heat at the front-end portion is reduced.

What is claimed is:

1. An endoscope comprising:
an imaging system; and
an illumination system,
wherein:
the illumination system includes a light guide and at least one illumination lens,
the imaging system includes an objective lens unit and an image pickup element,
when a direction along a long side of the image pickup element is set to be a first direction, and a direction along a short side of the image pickup element is set to be a second direction, the illumination system is disposed at a position shifted in the second direction with respect to the imaging system, and
the endoscope satisfies the following conditional expressions (1), (2), and (3):

$$1.35 < A \quad (1),$$

$$1 < L_H/L_V \quad (2), \text{ and}$$

$$1.5 < (r_V - L_V)/(r_H - L_H) \leq 3.17 \quad (3),$$

where:
A denotes a value calculated by the following expression when an aspect ratio long side:short side of an area of the image pickup element corresponding to a display image range is set to be H:V $A = H/V,$ $L_H$ denotes a dimension corresponding to the first direction of an end surface on an illumination lens side of the light guide,
$L_V$ denotes a dimension corresponding to the second direction of the end surface on the illumination lens side of the light guide,
$r_H$ denotes an outer-diameter dimension corresponding to the first direction of the illumination lens, and
$r_V$ denotes an outer-diameter dimension corresponding to the second direction of the illumination lens.

2. The endoscope according to claim 1, wherein the endoscope satisfies the following conditional expression (4):

$$1 < L_H/L_V < 1.5 \quad (4),$$

where:
$L_H$ denotes the dimension corresponding to the first direction of the end surface on the illumination lens side of the light guide, and
$L_V$ denotes the dimension corresponding to the second direction of the end surface on the illumination lens side of the light guide.

3. The endoscope according to claim 1, wherein the illumination lens is circular-shaped.

* * * * *